United States Patent
Clark et al.

(10) Patent No.: US 9,481,716 B2
(45) Date of Patent: Nov. 1, 2016

(54) TREATMENT FOR PEANUT ALLERGY

(75) Inventors: Andrew Clark, Cambridge (GB);
Pamela Ewan, Cambridge (GB)

(73) Assignee: Cambridge Univeristy Hospitals NHS Foundation Trust, Cambridge (GB)

( * ) Notice: Subject to any disclaimer, the term of this patent is extended or adjusted under 35 U.S.C. 154(b) by 115 days.

(21) Appl. No.: 14/005,789

(22) PCT Filed: Mar. 16, 2012

(86) PCT No.: PCT/GB2012/050584
§ 371 (c)(1),
(2), (4) Date: Nov. 27, 2013

(87) PCT Pub. No.: WO2012/123759
PCT Pub. Date: Sep. 20, 2012

(65) Prior Publication Data
US 2014/0093541 A1    Apr. 3, 2014

(30) Foreign Application Priority Data
Mar. 17, 2011   (GB) .................................. 1104537.4

(51) Int. Cl.
*A01N 65/00* (2009.01)
*A61K 36/00* (2006.01)
*A61K 36/48* (2006.01)
*A61K 39/35* (2006.01)
*A61K 39/36* (2006.01)
*C07K 14/415* (2006.01)
*A61K 39/00* (2006.01)

(52) U.S. Cl.
CPC ............ *C07K 14/415* (2013.01); *A61K 39/35* (2013.01); *A61K 2039/542* (2013.01); *A61K 2039/545* (2013.01)

(58) Field of Classification Search
None
See application file for complete search history.

(56) References Cited

U.S. PATENT DOCUMENTS

2004/0166123 A1*  8/2004  Jacobi et al. .............. 424/275.1

OTHER PUBLICATIONS

Anagnostou et al., "Efficacy and safety of high-dose peanut oral immunotherapy with factors predicting outcome," *Clin. Exp. Allergy* vol. 41, No. 9, pp. 1273-1281, 2011.

Blumchen et al., "Oral peanut immunotherapy in children with peanut anaphylaxis," *J. Allergy Clin. Immunol.* vol. 126, No. 1, pp. 83-91, 2010.

Cambridge University Hospitals NHS Foundation Trust: "Efficacy and Safety of High-dose Peanut Oral Immunotherapy With Factors Predicting Outcome," http://clinicaltrials.gov/arcive/NCT01259804/2010_12_13, 2010 [retrieved on Apr. 25, 2012] (2 pages).

Cambridge University Hospitals NHS Foundation Trust, "Study of Tolerance to Oral Peanut (STOP)," http://clinicaltrials.gov/ct2/show/NCT01259804, 2010 [retrieved on Apr. 25, 2012] (3 pages).

Clark et al., "Successful oral tolerance induction in severe peanut allergy," *Allergy* vol. 64, No. 8, pages 1218-1220, 2009.

Hofmann et al., "Safety of a peanut oral immunotherapy protocol in children with peanut allergy," *J. Allergy Clin. Immunol.* vol. 124, No. 2, pp. 286-291, 2009.

Jones et al., "Clinical efficacy and immune regulation with peanut oral immunotherapy," *J. Allergy Clin. Immunol.* vol. 124, No. 2, pp. 292-300, 2009.

Tang, "Oral immunotherapy for food allergy." *Current Allergy and Asthma Reports* vol. 9, No. 1, pp. 43-49, 2009.

Varshney et al., "A randomized controlled study of peanut oral immunotherapy: clinical desensitization and modulation of the allergic response," *J. Allergy Clin. Immunol.* vol. 127, No. 3, pp. 654-660, 2011.

* cited by examiner

*Primary Examiner* — Nora Rooney
(74) *Attorney, Agent, or Firm* — Klarquist Sparkman, LLP.

(57) ABSTRACT

The present invention relates to oral immunotherapy for the desensitization of patients who are hypersensitive to peanut allergen. The immunotherapy comprises increasing the oral dose daily dose of peanut protein administered to the patient at intervals of at least 2 weeks in a series of increments from an initial dose to a maximum dose, the series of dose increments including 2 mg, 5 mg, 12.5 mg, 25 mg, 50 mg, 100 mg, 200 mg, 400 mg and 800 mg; administering a daily oral dose of the maximum dose of peanut protein for at least 2 years and then administering a weekly oral dose of the maximum dose of peanut protein for at least 2 years.

5 Claims, 4 Drawing Sheets

TREATMENT FOR PEANUT ALLERGY

CROSS REFERENCE TO RELATED APPLICATIONS

This is the U.S. National Stage of International Application No. PCT/GB2012/050584, filed Mar. 16, 2012, which was published in English under PCT Article 21(2), which in turn claims the benefit of GB Application No. 1104537.4, filed Mar. 17, 2011, which is incorporated herein by reference in its entirety.

This invention relates to the treatment of peanut allergy by oral immunotherapy (OIT).

Peanut allergy is common, affecting 1-2% of young children in Europe and the USA [1-3], and unlike other common childhood food allergies (e.g. to hen's egg), resolution is uncommon [4]. The quality of life of the affected families is reduced because of constant fear over food choices and the likelihood of anaphylaxis [5, 6]. Despite the current best management, families of peanut allergic children have poor knowledge of how to avoid and also treat food allergy emergencies [7]. Accidental reactions are common (annual incidence rates for accidental reactions of 3, 14, and 50% have been reported in large studies [8]) Nearly one third of nut-allergic children cannot recognise the nut to which they are allergic—this lack of recognition puts them at increased risk of unintentional ingestion [9]. There is therefore a need to develop a disease-modifying therapy for peanut allergy.

Immunotherapy for inhalant and stinging insect allergy by subcutaneous injection has proven efficacy and safety. An early study of subcutaneous immunotherapy for peanut allergy showed a trend to benefit but was terminated after a severe adverse reaction [10]. Oral immunotherapy (OIT) for the treatment of persistent hen's egg and cow's milk allergy has been studied [11, 12]. Sublingual immunotherapy with hazelnut extract was studied in a small group of subjects with hazelnut allergy demonstrating an increase in dose threshold [13]. Two recently published studies of peanut oral immunotherapy employing an initial rush protocol showed poor tolerability of the rush period, with better efficacy after a period of gradual dose escalation [14-16].

A small trial of peanut oral immunotherapy using an initial dose matched to the patient's challenge threshold and gradual dose escalation has previously been reported [17].

The present inventors have developed an improved method of oral immunotherapy to desensitise patients who are hypersensitive to peanut allergen.

One Aspect of the Invention Provides a Method of Treating an Individual with Peanut Allergy which Comprises:
(1) providing an individual with peanut allergy,
(2) orally administering a daily dose of peanut protein to the patient,
 wherein the daily oral dose is increased at intervals of at least 2 weeks in a series of increments from an initial dose to a maximum dose, the series of dose increments including 2 mg, 5 mg, 12.5 mg, 25 mg, 50 mg, 100 mg, 200 mg, 400 mg and 800 mg,
(3) orally administering a daily dose of the maximum dose of peanut protein for at least 2 years,
(4) orally administering a weekly dose of the maximum dose of peanut protein for at least 2 years.

A patient with a peanut allergy may display an immediate type-1 hypersensitivity immune reaction on exposure to peanuts or peanut extract.

Peanuts (*Arachis hypogaea*) contain multiple allergenic proteins, including Ara h1 to Ara h9 (see for example, Sicherer S H et al J Allergy Clin Immunol. 2007; 120:491-503, de Leon et al Expert Rev Mol Med 2007 9 (1) 1-18). An individual with a peanut allergy may be hypersensitive to one or more of these allergenic peanut proteins.

Patients who are hypersensitive to any peanut allergen or combination of peanut allergens may be treated using the methods described herein.

Individuals with peanut allergy from Western European populations are typically hypersensitive to one or more of Ara h1, h2 and h3 and most individuals display an allergic response to Ara h2. However, other patterns of peanut allergen hypersensitivity may be more typical in individuals from other populations.

A patient with a peanut allergy may display peanut-specific serum IgE, i.e. IgE which specifically binds to peanut protein.

Patients may be diagnosed with peanut allergy according to standard clinical criteria. Standard clinical criteria may include for example, a history of a type-1 hypersensitivity reaction which is temporally related to peanut ingestion (e.g. hives, swelling, wheezing, abdominal pain, vomiting, breathlessness), and the presence of peanut-specific IgE by positive skin prick test (wheal diameter$>$/=3 mm) or ImmunoCap serum IgE$>$0.35 kU/l.

The methods described herein may be used for any patient with peanut allergy and are independent of the patient's sensitivity or challenge threshold to peanut allergen, the weight or height of the patient and other factors.

Peanut protein is the total protein contents of a peanut and contains all allergenic peanut proteins, including Ara h1 to h9. Peanut protein may be administered in the form of a whole or part peanut, or it may be extracted, isolated and/or purified from a peanut. For example, peanut protein may be provided as a peanut extract, such as peanut flour.

Peanut flour is produced by crushing, grinding and/or milling whole peanuts. The flour may be partially or completely defatted to reduce the fat content. Defatting does not affect the allergenic peanut protein content of the flour.

The peanut protein content of peanut flour may be readily determined using standard techniques and is typically 50% (w/w) peanut protein. Peanut flour is widely available from commercial sources (e.g. Golden Peanut Company GA USA).

Other peanut extracts which contain peanut protein may also used in the methods described herein.

In some embodiments, total peanut protein may isolated and/or purified from other constituents of peanuts for use as described herein.

In some embodiments, peanut protein may be administered as a whole peanut. This may be preferred, for example, for high incremental doses of peanut protein, such as 400 mg and 800 mg.

Peanut protein represents 25% (w/w) of a peanut and the average weight of a peanut is 500-650 mg. An incremental dose of 400 mg may be administered as 2-3 large peanuts, and an incremental dose of 800 mg may be administered as five large peanuts.

Suitable whole peanuts include any form of roasted peanut, including salted and honey roast, and coated or embedded peanuts, for example peanuts coated or embedded in a food product, such as chocolate or yoghurt.

In some embodiments, peanuts which constitute the incremental dose of peanut protein may be crushed and presented inside a food product, such as a small biscuit, cake, chocolate, sweet or jam.

Conveniently, peanut protein, optionally in the form of peanut flour, may be mixed with a carrier to produce a composition for administration to the patient.

Suitable carriers mask the peanut protein from the mouth and upper gastrointestinal (GI) tract and reduce or prevent local itching/swelling reactions in these regions during administration. For example, a carrier may contain one or more lipid, polysaccharide or protein constituents.

The carrier may be a food product, for example a dairy or dairy substitute product, such as yoghurt, milkshake or chocolate, or another food product with similar properties. Dairy substitute products may include soy-based products.

In some embodiments, the composition for administration may be a food product which has been supplemented with peanut protein, for example in the form of peanut flour.

The composition may be any food product which can be produced with a discrete dose of peanut protein, e.g. chocolate, yoghurt, confectionery (e.g. sweets and jellies) or beverages. In some embodiments, the composition may be a cooked or baked food product, such as a biscuit or cake.

The peanut protein may be added at any stage of the production of the food product.

The food product may be supplemented with flavourings to mask the taste of the peanut protein. Suitable food flavourings are well-known in the art and include sugar, mint, vanilla and orange essence.

The food product may be supplemented with preservatives, stabilizing agents, fillers, colourings and sweeteners in accordance with standard food production techniques.

In other embodiments, the composition for administration may be an oral delivery vehicle such as a capsule, cachet or tablet, each of which contains a predetermined amount of peanut protein to provide the correct incremental dose to the patient. Oral delivery vehicles may be useful, for example, in avoiding contact between the peanut protein and the mouth and upper gastrointestinal tract. Suitable carriers, binders, fillers or diluents lubricants and preservatives for use in oral delivery vehicle are well known in the art.

In some embodiments, the composition for administration may further comprise other components, for example, anti-allergy drugs, such as antihistamines, steroids, bronchodilators, leukotriene stabilisers and mast cell stabilisers. Suitable anti-allergy drugs are well known in the art. This may be useful in reducing allergic inflammation and increasing tolerance of the peanut protein.

As described below, compositions, such as food products, for use as described herein may be formulated in unit dose formulations which contain a defined amount of peanut protein.

The initial dose of peanut protein which is administered to the individual is 2 mg or less. For example, the initial dose may be 0.5 mg, 1 mg or 2 mg, most preferably 2 mg.

As described above, the series of increments through which the daily dosage of the peanut protein may be increased may include 2 mg, 5 mg, 12.5 mg, 25 mg, 50 mg, 100 mg, 200 mg, 400 mg and 800 mg.

Optionally, the initial daily dose of peanut protein may be less then 2 mg. The daily dose may then be progressively increased, for example by at intervals of at least every two weeks in one, two or more increments to 2 mg and then increased at least every two weeks in the above sequential increments. For example, the 2 mg dose in the above sequential incremental doses may be preceded by dose increments of 0.5 and 1 mg or a dose increment of 1 mg. In other words, an initial dose of 0.5 mg may be incrementally increased to 1 mg after at least 2 weeks, and then 2 mg and then as described above. An initial dose of 1 mg may be incrementally increased to 2 mg after at least 2 weeks and then as described above.

For example, the daily oral dose of peanut protein may be increased at intervals of at least 2 weeks in a series of increments which consist of:
1) 2 mg, 5 mg, 12.5 mg, 25 mg, 50 mg, 100 mg, 200 mg, 400 mg and 800 mg,
2) 0.5 mg, 1 mg, 2 mg, 5 mg, 12.5 mg, 25 mg, 50 mg, 100 mg, 200 mg, 400 mg and 800 mg; or
3) 1 mg, 2 mg, 5 mg, 12.5 mg, 25 mg, 50 mg, 100 mg, 200 mg, 400 mg and 800 mg.

In preferred embodiments, the daily oral dose of peanut protein may be increased at intervals of at least 2 weeks in a series of increments which consist of 2 mg, 5 mg, 12.5 mg, 25 mg, 50 mg, 100 mg, 200 mg, 400 mg and 800 mg.

The daily oral dose may be increased after two weeks at a dose increment, if the patient has not suffered from repeated adverse allergic reactions, required anti-allergy treatment suffered from concurrent illness or received a vaccination during the second week of administration of the dose increment.

Adverse allergic reactions may include acute exacerbation of allergic signs or symptoms.

If the individual has suffered from an adverse allergic reaction, received anti-allergy treatment or suffered from a concurrent illness during the second week at a dose increment, then the same dose increment may be maintained for 2 additional weeks before further incremental dose increases.

The individual may be monitored for adverse reactions for 2 hours following the first administration of each incremental dose of peanut protein. For example, the patient may be assessed prior to administration and parameters such as pulse, blood pressure, peak expiratory flow rate in 1 second and oxygen saturation measured. The increased incremental dose is then administered and the patient monitored for the development of allergic symptoms and/or changes in any of the measured parameters. Allergic symptoms may be treated with conventional medication as required.

If an individual suffers a severe adverse reaction to the first administration of an incremental dose of peanut protein, for example wheezing or other allergic symptoms assessed as serious by a clinician, the daily dose may be reduced to the previous incremental dose. After 2 weeks at the previous incremental dose, the dose may then be increased again to the next incremental dose.

The maximum dose of peanut protein which is administered may be 800 mg or less. Preferably, the maximum dose is 800 mg. Some individuals may be unable to tolerate a dose of 800 mg, in which case the maximum dose may be less than 800 mg, for example the highest incremental dose which is tolerated by the individual, such as 400 mg or 200 mg.

An individual may be considered not to tolerate an incremental dose of peanut protein if significant allergic symptoms occur after 14 consecutive days of administration of the incremental dose. Significant allergic symptoms include abdominal pair lasting for more than 20 minutes, wheezing, throat tightening, and nausea/vomiting.

The maximum dose of peanut protein may be administered daily for a period of at least 1 year, at least 1.5 years or at least 2 years.

After the patient has taken the maximum dose of peanut protein daily for this period and has demonstrated good tolerance to the daily dose (e.g. no allergic reactions to doses in the past 3 months), administration of the maximum dose of peanut protein may be switched to a weekly regime. For example, the maximum dose of peanut protein may then be administered weekly for at least 2 years, at least 2.5 years or at least 3 years.

A method as described herein may comprise measuring the level of anti-peanut IgE in the serum of the patient or by skin prick test.

The level of anti-peanut IgE may be measured before the administration of the initial dose of peanut protein.

Anti-peanut IgE levels in a patient before treatment may be predictive of the amount of desensitisation which may occur. For example, low levels of anti-peanut IgE may be indicative that the treatment will be well tolerated and effective in the individual, for example there may be fewer dose alterations due to reduced tolerance (preferably none) and the patient is more likely to tolerate a larger amount of peanut, if they were to be challenged after the treatment. In some embodiments, the number of incremental dosages required to reach the maximum dose of peanut protein may be reduced for individuals with low initial levels of anti-peanut IgE.

The level of anti-peanut IgE may be measured during the updosing phase (step 2) and/or the maintenance phase of the treatment (steps 3 and 4).

Anti-peanut IgE is a surrogate marker for clinical peanut reactivity and may be indicative of the efficacy of the treatment. Typically, the level of anti-peanut IgE rises initially during the treatment described herein and then gradually drops to low levels. Following the treatment, levels of anti-peanut IgE may be reduced or abolished.

Weekly administration of the maximum incremental dose may continue until the anti-peanut IgE level in the patient serum is minimised and the patient is no longer reactive to peanut protein. For example, anti-peanut IgE levels may be reduced to zero, substantially zero, or very low levels.

In some embodiments, the level of IgE reactive to specific allergens, such as Ara h2, may be measured in the serum of the patient.

Methods described herein may be useful in the treatment of peanut allergy. For example, the sensitivity of the patient to peanut protein may be reduced or abolished following the treatment. For example, the maximum oral dose of peanut allergen which is tolerated by a patient without the onset of allergic symptoms, or the median maximum oral dose of peanut allergen which is tolerated by a population of patients, may be increased by at least 50 fold, at least 500 fold, at least 750 fold or at least 1000 fold after the treatment relative to before the treatment.

The methods described herein may be useful in treating a population or cohort of patients with peanut allergy. A method of treating a population of patients with peanut allergy may comprise:
  (1) providing a population of patients with peanut allergy,
  (2) administering to the population of patients a daily oral dose of peanut allergen,
    wherein the daily oral dose is increased at intervals of at least 2 weeks in a series of increments from an initial dose to a maximum dose, the series of dose increments including 2 mg, 5 mg, 12.5 mg, 25 mg, 50 mg, 100 mg, 200 mg, 400 mg and 800 mg,
  (3) orally administering daily to the population the maximum dose of peanut protein for at least 2 years, following step 2,
  (4) orally administering weekly to the population the maximum dose of peanut protein for at least 2 years following step 3.

As described above, preferably, the initial dose administered to the population is 2 mg and the maximum dose is 800 mg and the series of dose increments consists of 2 mg, 5 mg, 12.5 mg, 25 mg, 50 mg, 100 mg, 200 mg, 400 mg and 800 mg.

Methods of the invention may also be useful in testing compounds for the treatment of allergy and allergic symptoms. For example, the effect of a test compound, such as a putative immunosuppressive or anti-allergy compound, including anti-IgE, antihistamine, steroid, bronchodilator, leukotriene stabiliser or mast cell stabiliser, on the treatment of a population of patients with peanut allergy as described above may be determined. For example, a test compound may be administered to the patients before, during or after the administration of the peanut protein and the effect of the test compound on how well the peanut protein is tolerated by the patient (as assessed by frequency and severity of reactions) and the level of anti-peanut IgE during the treatment may be determined.

Other aspects of the invention provide a therapeutic composition comprising peanut protein for use in a method of treating peanut allergy, as described above, and the use of peanut protein in then manufacture of a medicament for use in a method of treating peanut allergy, as described above.

A suitable therapeutic composition may be provided in unit dosage form and may contain a defined amount of peanut protein, for example a dose selected from 0.5 mg, 1 mg, 2 mg, 5 mg, 12.5 mg, 25 mg, 50 mg, 100 mg, 200 mg, 400 mg and 800 mg, preferably a dose selected from 2 mg, 5 mg, 12.5 mg, 25 mg, 50 mg, 100 mg, 200 mg, 400 mg and 800 mg.

Another aspect of the invention provides a set of therapeutic compositions, the set comprising multiple individual unit dose formulations comprising peanut protein,
  wherein the amount of peanut protein in each unit dosage formulation in the set is identical and is selected from 0.5 mg, 1 mg, 2 mg, 5 mg, 12.5 mg, 25 mg, 50 mg, 100 mg, 200 mg, 400 mg and 800 mg; more preferably 2 mg, 5 mg, 12.5 mg, 25 mg, 50 mg, 100 mg, 200 mg, 400 mg and 800 mg.

The set may comprise 5 or more, 10 or more, 14 or more, 15 or more, 20 or more, 25 or more, 30 or more or 35 or more unit dose formulations. In some embodiments, the set may comprise unit dose formulations sufficient for two, three or four weeks administration of the incremental dose, for example, 14, 21 or 28 unit dose formulations.

A set may further comprise up to 10, for example 4 or 5 additional unit dose formulations as a precaution against the patient running out.

The set of therapeutic compositions may be used as a medicament, for example in a method of treating peanut allergy, as described above or may be used in the manufacture of a medicament for use in a method of treating peanut allergy, as described above.

The unit dose formulations may be separately packaged in sealed units, for example to protect the contents from the external environment. The unit dose formulations may be packaged in separate sealed containers, for example wrappers, pouches, bags, cartons, capsules, sachets, vials or tubes.

Each unit dose formulation may comprise a single dose of the peanut allergen. Typically, for use in steps 1) to 3), the single dose is a single daily dose. For use in step 4), the single dose may be a single weekly dose. For example, a unit dose formulation may contain a weekly dose of 800 mg of peanut protein.

Another aspect of the invention provides a group of sets of therapeutic compositions as described above. For example, a group of sets of therapeutic compositions, wherein each set in the group comprises multiple separate unit dose formulations comprising peanut protein and each unit dosage formulation in the set comprises an identical amount of peanut protein, and wherein the group includes sets with unit dosage formulations which contain 2 mg, 5 mg, 12.5 mg, 25 mg, 50 mg, 100 mg, 200 mg, 400 mg and 800 mg of peanut protein.

The group may further include sets with unit dosage formulations which contain 0.5 mg and/or 1 mg peanut protein.

The group of sets of therapeutic compositions may be used as a medicament, for example in a method of treating peanut allergy, as described above or may be used in the manufacture of a medicament for use in a method of treating peanut allergy, as described above.

A group of sets of therapeutic compositions may comprise two, three, four, five, six, seven, eight or nine or more sets of unit formulations. For example, the group may comprise sets of unit dosage formulations which contain 2 mg, 5 mg, 12.5 mg, 25 mg, 50 mg, 100 mg, 200 mg, 400 mg and 800 mg of peanut protein.

Peanut protein and suitable formulations of peanut protein are described in more detail above.

Sets and groups of sets of compositions may be individually packaged.

Other aspects of the invention relate to the formulations comprising peanut protein for use in the maintenance phase of a method described above.

For example, a set of unit dosage formulations, each unit dosage formulation containing 800 mg of peanut protein, may be used in a method which comprises;

(1) providing a patient with peanut allergy who has been treated, as described above, by administration of a daily oral dose of peanut protein, wherein the daily oral dose has been increased at intervals of at least 2 weeks in a series of increments from an initial dose to a dose of 800 mg of peanut protein, the series of dose increments including 2 mg, 5 mg, 12.5 mg, 25 mg, 50 mg, 100 mg, 200 mg, 400 mg and 800 mg, (2) orally administering the dosage formulation containing 800 mg of peanut protein daily for at least 2 years to said patient, and (3) administering the dosage formulation containing 800 mg of peanut protein weekly for at least 2 years following step 2.

Various further aspects and embodiments of the present invention will be apparent to those skilled in the art in view of the present disclosure.

All documents mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures and tables described below.

EXPERIMENTS

Methods #1

Figure 1:
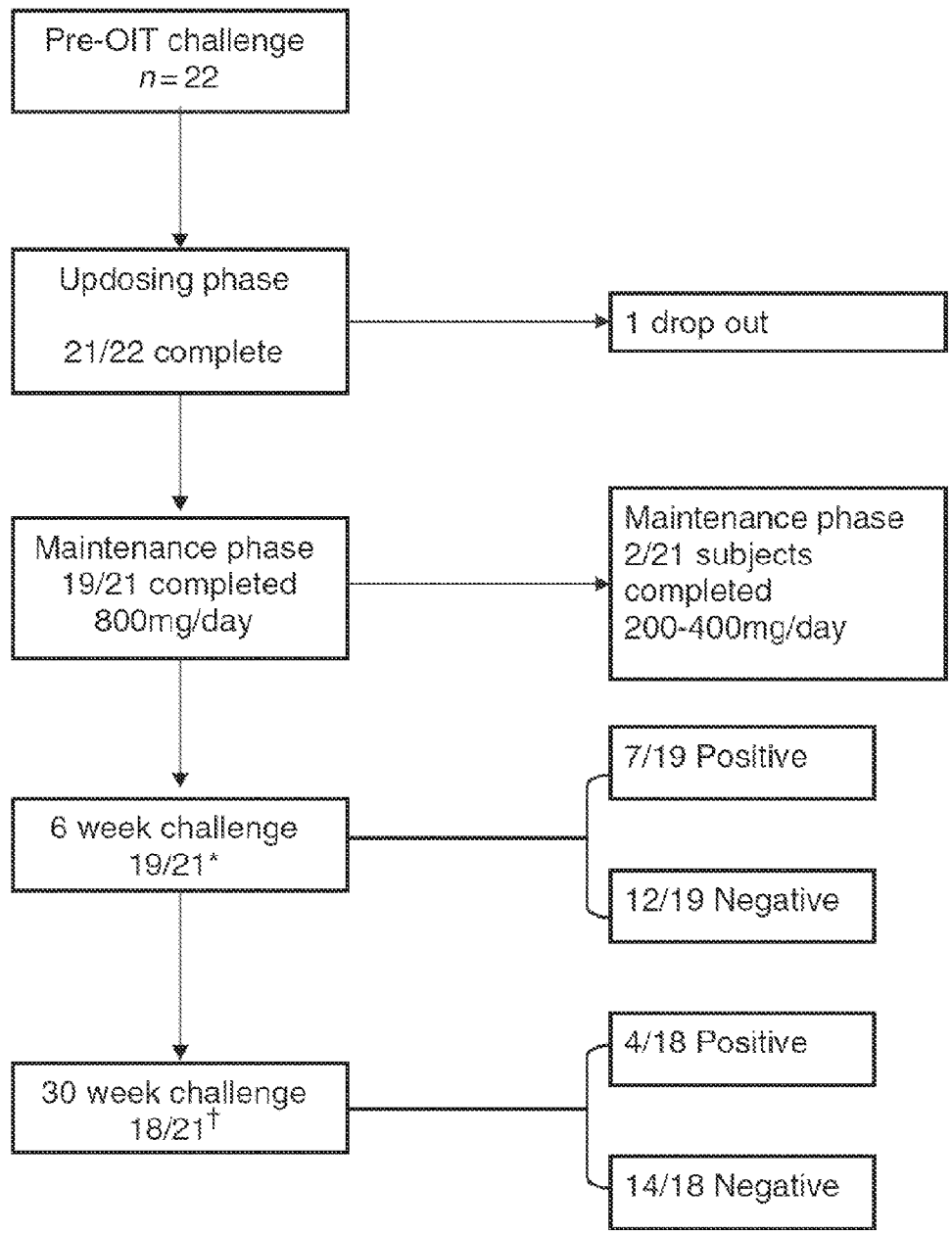
FIG. 1 shows a flow diagram of an OIT trial described herein.

This study was approved by the Local Ethics and Research and Development Committees and each family gave written informed consent. Inclusion criteria were a positive peanut oral challenge and presence of peanut specific IgE in children aged 4-18 yrs. Major immunodeficiency and an inability to comply with the study protocol were exclusion criteria. Twenty-two children were enrolled. Children with a history of anaphylaxis after peanut ingestion were included.

Skin prick tests (SPTs) were performed (peanut extract, saline negative and histamine 10 mg/ml positive controls; single point lancets; ALK-Abello, HØrsholm Denmark) and peanut SPT was interpreted as positive when the wheal diameter was at least 3 mm greater than the negative control. Serum was analysed for whole peanut and Ara h 2-specific IgE (CAP-system FEIA; Phadia, Uppsala, Sweden).

Double-Blind Placebo-Controlled Food Challenges (DBPCFC)

DBPCFCs (low dose challenge protocol) were performed according to an international consensus statement [18]. Peanut was administered as ground and partially defatted peanut flour (50% protein, light roast; Golden Peanut Company, Alpharetta, Ga., USA). The carrier was a chocolate bar (32% fat) containing vegetable oil, sugar and orange essence (free of egg, milk, peanut, tree nuts and soya) and blinding was assured by a tasting panel. Placebo and active (peanut flour) doses were administered on separate days in random order, and dose intervals were at least 30 min. A challenge dose regime including 1, 5, 50, and 500 mg of peanut protein was piloted for the first subject. The dose range was subsequently modified to 1, 5, 25, 50, 75 and 100 mg of peanut protein. The challenge was scored positive if a) objective symptoms occurred or b) subjective symptoms occurred on at least two consecutive doses. A negative DBPCFC was followed by an open challenge with a cumulative dose of 6 peanuts (approximately 900 mg protein). Overall, the challenge was scored negative if there was no reaction to the DBPCFC or open challenges [18]. Pre-intervention challenges were used to both confirm the presence of clinical allergy to peanut and identify the highest amount of protein tolerated before a reaction occurred (highest tolerated dose).

Oral Immunotherapy (OIT)

OIT was administered in two phases, firstly there was a gradual updosing phase with two-weekly increments to 800 mg/day, followed by a maintenance phase where the highest tolerated dose (with a target of 800 mg/day) was taken continuously for 30 weeks. The same peanut flour used in the challenges was also used for updosing. The updosing phase increments were 0.5 mg, 1 mg, 2 mg, 5 mg, 12 mg, 25 mg, 50 mg, 100 mg, 200 mg, 400 mg and 800 mg peanut protein.

Starting doses for immunotherapy were below the subject's own pre-OIT threshold. All dose increases took place in the Wellcome Trust Clinical Research Facility and subjects were observed for 2 h. The same dose was administered at home daily for 2 weeks. At the final updose, subjects were given the choice of continuing to take peanut flour or 5-7 peanuts daily (~800 mg protein).

Participating families were advised to record and report any symptoms which occurred during the course of the intervention. Families were provided with oral antihistamines, an epinephrine auto-injector and a treatment plan, with training [8]. Participants were asked to avoid any other source of peanut in their diet.

Children were asked to take their dose with food and instructed not to exercise for 1-2 hours after taking a dose. Families had 24 hour access to the study team by telephone. If reactions occurred that were troublesome, the OIT dose was reduced to the previous tolerated dose for 1-2 weeks before being increased again. Reactions were recorded and categorized according to a published grading system [8].

Post OIT Challenges

An open peanut challenge using weighed roasted peanuts was performed after completing six weeks of the maintenance phase (2.6 g peanut protein-dose intervals: 0.8 g, 0.45 g, 0.45 g, 0.45 g, 0.45 g protein; a total of approximately 12 peanuts). A further peanut challenge was undertaken after completing 30 weeks of the maintenance phase (6.6 g protein-8 equal dose intervals of 0.83 g protein; a total of approximately 32 peanuts). Dosing intervals were 20-30 mins and the same criteria for scoring the challenges was used as for the pre-OIT challenge.

Statistics

Medians of non-parametric data sets were compared with Mann-Whitney U test. Means of normally distributed data were compared with student's t test. Comparison between multiple non-parametric data sets was made with Kruskall-Wallis test and Dunn's post test comparison. Wilcoxon Ranked pairs test was applied to paired non-parametric data. Data were analysed using Graphpad Prism (v5.0) San Diego, Calif., USA.

Methods #2

Potential patients were assessed to determine their suitability for undertaking peanut immunotherapy. Patients who meet the following criteria were eligible:
1. Typical clinical history of an immediate type-1 hypersensitivity reaction to a peanut-containing food.
2. Presence of peanut-specific IgE detected either in the serum (e.g. ImmunoCap peanut IgE>0.35 kU/l) or by skin prick test wheal diameter>3 mm.

Peanut oral immunotherapy was not be undertaken in patients with a history of anaphylaxis to peanut which resulted in hypotension, or required multiple adrenaline injections, or required admission to an intensive care unit.

Immunotherapy up-dosing was undertaken if the following criteria have been met: The subject has had no acute exacerbation of allergic signs or symptoms within the last week, has not received short-acting beta-2 agonists for 12 hours (asthma should be well controlled), long-acting beta-2 agonists for 24 hours, short-acting antihistamines in the last 48 hours, or long-acting antihistamines in the last 7 days. The subject has no concurrent illness.

Patients received daily doses of peanut protein starting at 2 mg per day. This was given as peanut flour (50% protein) and was mixed into a carrier which is known to be tolerated (e.g. yoghurt). The first dose was administered in a hospital day unit followed by a 2 hour observation period. Subsequently doses were taken daily at home by participants. Every 2 weeks subjects returned to the day unit for a dose increase and 2 hours of observation. The dose increments were 2 mg, 5 mg, 12.5 mg, 25 mg, 50 mg, 100 mg, 200 mg, 400 and 800 mg. The final dose (or if this was not tolerated, the highest tolerated dose) was taken daily for at least 2 years from the start date of treatment. Following this the dosing frequency may be reduced to once weekly for a period of three to five years.

Each patient was provided with:
Symptom advice sheet (containing advice to avoid strenuous exercise for 2 hours after home dose)
Contact information for clinical team
Non-sedating oral antihistamine and injectable adrenaline device
Training on adrenaline autoinjector use
Emergency treatment plan
Patients are asked to complete a symptom diary, noting type and duration of symptoms and any exacerbating factors (e.g. exercise, excessive tiredness, systemic illness).

If symptoms were experienced during updosing on the day unit then the following actions were performed:
If wheeze/breathlessness/reduced PEFR/vomiting occur then provided the next lowest dose for daily treatment. Contacted daily to reassess.
If mild abdominal pain, oral itching or urticaria occurred then provided reassurance and continued the current dose. Contacted daily to reassess.
If other symptoms occurred that are intolerable to the subject that the dose was also be reduced at the supervising clinician's discretion.

If any symptoms were experienced by participants at home, families were advised to contact the clinical team. The following assessments and advice were provided as indicated:
If wheeze/breathlessness/vomiting occur within 2 hours of a single dose taken at home then reduce the dose to the next lowest, and contact daily to reassess.
If abdominal pain/rhinitis/oral itching occurs within 2 hours of a single dose taken at home then continue with the current dose and contact daily to reassess.
If episodes of abdominal pain/rhinitis/oral itching occur every day for 10 days, then reduce to the next lowest daily and contact daily to reassess.
After a dose reduction, attempt to increase dose again as per protocol.

Intercurrent illness, if symptoms occur which are not temporally related to taking a dose (for example, but not limited to wheeze, rhinitis, vomiting, fever, diarrhoea or rash) occurring more that 2 hours after a dose then consider reducing dose and advise to seek medical consultation, contact daily to reassess.

Results

Study Population 22 children aged 4-18 yrs were enrolled, with a median age of 11 yrs. Demographic features are summarized in table 1.

Pre-Immunotherapy Peanut Challenge

All 22 subjects had a positive DBPCFC (for explanation of subject flow see FIG. 1). The highest tolerated dose of peanut varied between 1 mg and 110 mg protein (median 6 mg—see table 2). Subject 12 had anaphylaxis during DBP-CFC. He developed rhinitis nausea, breathlessness, tightness in the chest, pallor and severe abdominal pain. He was promptly treated with intramuscular epinephrine, intravenous chlorphenamine and hydrocortisone. Four subjects passed the initial DBPCFC but they all developed objective symptoms during subsequent open peanut challenge. There were no screening failures.

Oral Immunotherapy

Updosing Phase

Oral immunotherapy up-dosing was commenced in 22 subjects, with 19 tolerating updosing to the planned maximum dose of 800 mg protein per day (FIG. 1). The amount of time required for updosing was 56-264 days (median 140d) and the mean number of attendances for updosing was 9.7 (95% CI 8.3-11.1). 8/22 (36%) required a transient dose reduction during updosing but were able to complete the schedule up to 800 mg protein as planned. One subject dropped out after the 1st updose at home having developed transient abdominal pain. There was no further contact. During updosing 6 subjects reported failure to take a dose. A total of 10 doses were missed on 9 separate occasions. No reactions occurred following missed doses.

Maintenance Phase

19/22 (86%) subjects successfully maintained desensitisation at the maximum dose of 800 mg protein for the remainder of the study (FIG. 1). Subjects 20 and 21 initially received 800 mg protein but subsequently required lower maintenance doses of 400 mg and 200 mg respectively after developing repeated transient episodes of oral itching and abdominal pain. These lower doses were well tolerated for the remainder of the study (30 weeks). Both subjects had high peanut specific IgE and also had protracted intercurrent illnesses during updosing and maintenance phases.

The difficulty in desensitisation did not appear to be related to threshold dose. Overall, there was no difference in median pre-OTT challenge threshold between those who required dose adjustments during OIT (and were more 'difficult' to desensitise) compared to those who did not.

Six Week Challenge

After completing six weeks of the maintenance phase, 19/22 (86%) subjects underwent challenge to 2.6 g protein. 18/19 (95%) ingested the full challenge dose, of those 12/19 (63%) had no symptoms and 7/19 (37%) developed mild/moderate symptoms. Symptoms included abdominal discomfort, rhinitis, facial erythema and lip angioedema. Subject 13 developed abdominal pain and the challenge was stopped at the request of the participant, after they had ingested 600 mg protein. Subjects 21 and 22 were not offered a challenge because they were not receiving the top maintenance dose (FIG. 1).

30 Week Challenge

Figure 2:
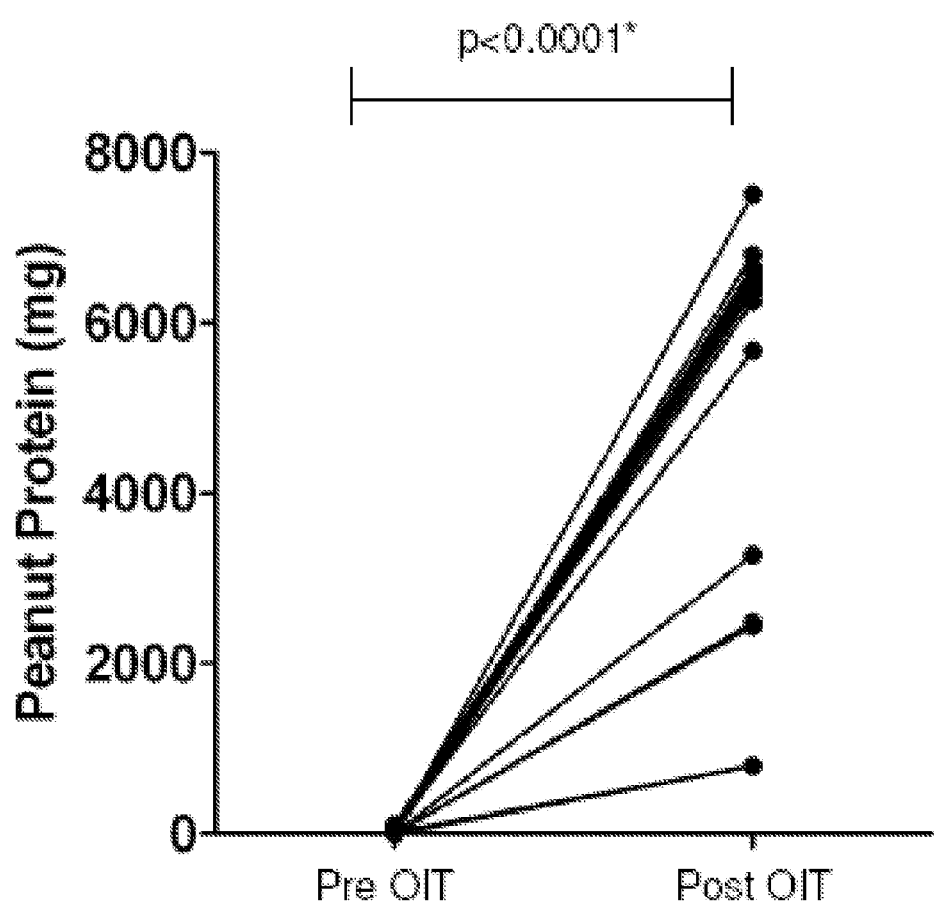
FIG. 2 shows the effect of OIT on the tolerated peanut protein dose in patients.

After completing 30 weeks of the maintenance phase, 18/22 (81%) subjects underwent a 6.6 g protein challenge. 14/18 (78%) subjects did not have any symptoms during the challenge. 4/18 (22%) experienced mild/moderate symptoms (mild abdominal discomfort and vomiting) having ingested all challenge doses. Subjects 13, 21 and 22 were not offered a challenge because they had either not passed the 6 week challenge or were not receiving the top maintenance dose Change in Tolerated Dose after Immunotherapy (FIG. 2)

The median highest amount of peanut tolerated during the pre-OIT challenges was 6 mg (range 1-110 mg). After updosing and maintenance the median highest tolerated dose during challenge (or immunotherapy if no challenge was applied) was 6469 mg (range 800 mg-7510 mg). For those who underwent immunotherapy, this represents at least a thousand-fold increase in median tolerated dose for the group.

Reactions During Immunotherapy

19/22 (86%) subjects developed transient allergic symptoms at some point during the updosing and maintenance phases. Allergic symptoms did not occur with every dose increase. The mean number of updosing periods where allergic symptoms occurred was 5.2 (95% CI 3.39-7.15) i.e. in about half the up dosing periods. The most common symptoms during the updosing phase were by far oral itching (14/22 64%) and/or abdominal pain (50%) whereas less often rhinoconjunctivitis (27%), wheeze (22%), nausea and vomiting (18%) occurred (see table 3). The majority of symptoms developed within 1 hr of taking the dose, lasted less than 1 hour and responded well to oral antihistamines and/or beta 2 agonists. 3/22 (14%) subjects did not have any symptoms during the up-dosing period.

Reactions with Extrinsic Factors (REFs)

During up-dosing 12/22 (54%) experienced unexpected transient and isolated reactions to a daily dose that had been taken for up to two weeks without reaction (table 4). The episodes were transient, usually lasting <1 hr and would occur on a single day, with the same dose being taken without reaction on subsequent days. These REFs occurred over a median period of 3.7 m from the start of immunotherapy (range 1.5-6.3 m).

Symptoms were usually mild-moderate and episodes were treated with antihistamines and/or inhaled beta-2-agonists (table 4). Intramuscular epinephrine was not required. REFs were associated with recognizable extrinsic factors such as exercise (up to 2 hours after taking a dose), infection (respiratory, varying from a cold to pneumonia or gastrointestinal), tiredness (caused by sleep deprivation), co-exposure to other allergens (i.e. pet dander), anxiety and/or menstruation (table 4).

Skin Prick Tests and Serum Specific IgE Levels

Figure 3A:
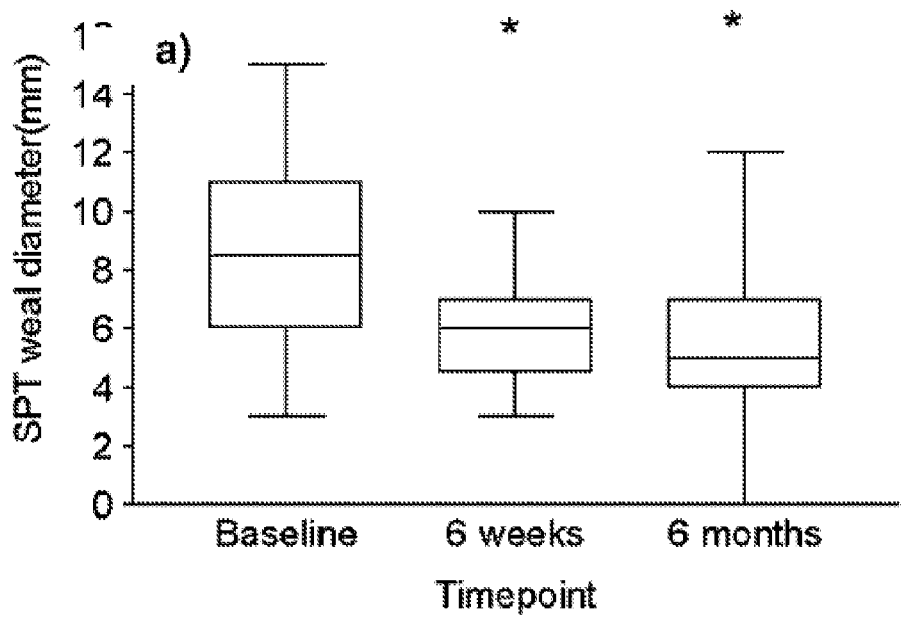
FIG. 3a shows skin prick test weal diameters in response to peanut extract after 6 and 30 weeks of OIT compared to baseline.
Figure 3B:
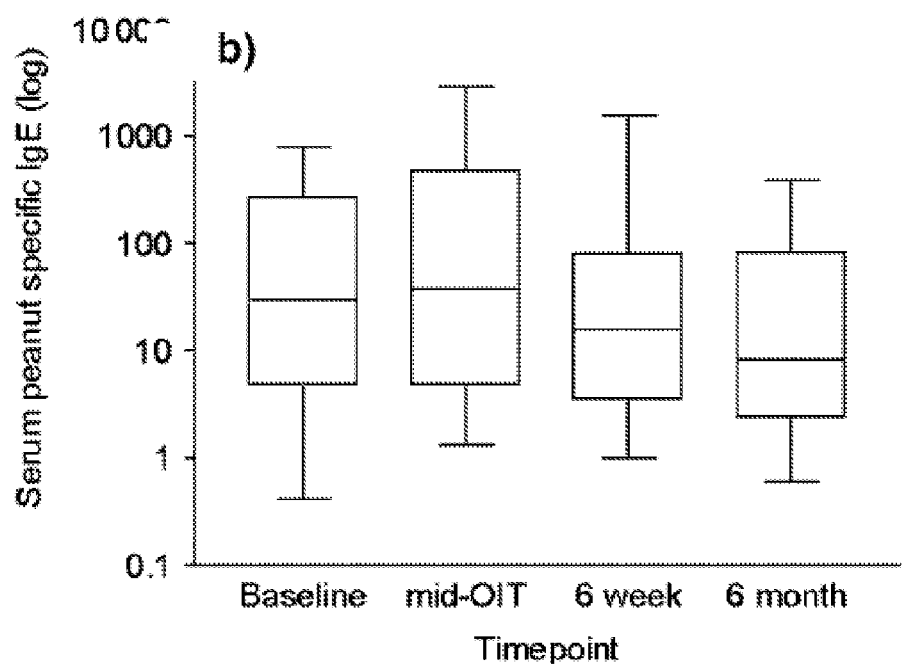
FIG. 3b shows serum anti-peanut IgE levels midway though OIT, and after 6 and 30 weeks of OIT compared to baseline.
Figure 4:
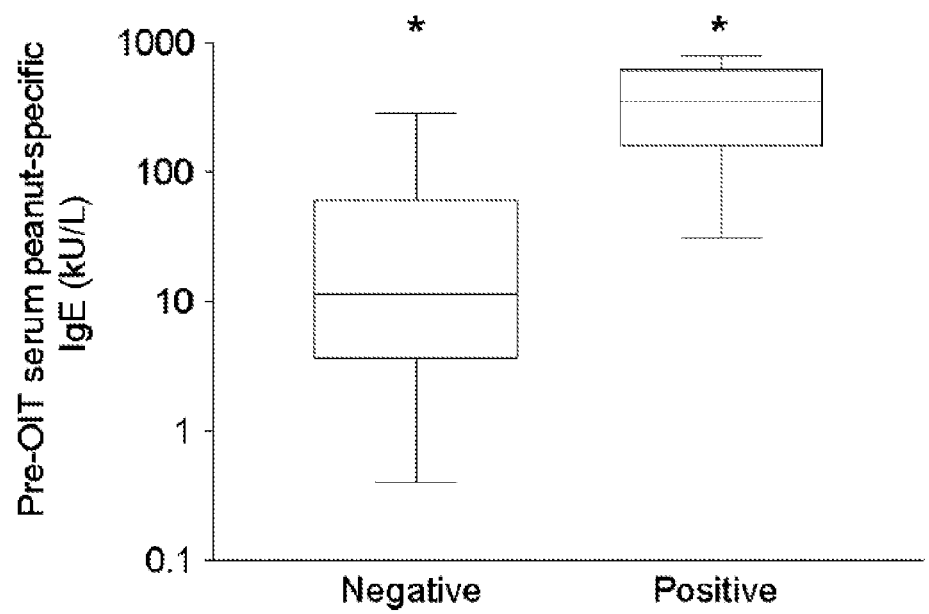
FIG. 4 shows pre-OIT serum anti-peanut IgE levels in patients who passed (n=14_) and failed (n=4) the 30 week challenge.

There was a significant reduction in skin prick test weal size to peanut extract at 6 and 30 weeks compared to baseline (FIG. 3a median 6 mm v 5 mm v 8.5 mm respectively). The median serum peanut specific IgE for the group showed a transient rise midway through OIT (38.3 kU/l), followed by a trend to reduction at 30 weeks (8.35 kU/l), compared to the pre-OIT value (29.7 kU/l) (FIG. 2b). Pre OIT peanut IgE was compared to the 'difficulty' in performing immunotherapy for each individual (measured as the number of episodes of dose reduction during OIT—table 2). We found that no subject (8/8) with a peanut IgE<27.3 kU/l required an alteration to their immunotherapy regime. In contrast 5/13 (39%) with a peanut IgE>/=27.3 kU/l required a dose reduction (p=0.0068; Fisher's exact test). In addition, median pre-OIT serum peanut IgE was significantly lowering those who passed the 30-week challenge (n=14) compared to those who failed (n=4) or did not attempt it due to reduced tolerance (n=3; n=1 drop out) (11.3 v 354.0 kU/l; *p=0.0625; Mann Whitney test; FIG. 4). Serum peanut. Ara h 2 IgE was also significantly reduced in the group who passed the 30-week challenge (table 5). We also compared the pre-OIT challenge threshold, age at enrolment, presence of current asthma and rhinitis between these groups and found no difference (table 5).

In this study of 4-18 year old peanut-allergic children, a gradual updose OIT regime resulted in a thousand-fold increase in the amount of peanut tolerated, with an acceptable safety profile. All subjects tolerated a maintenance dose well above their pre-treatment challenge threshold, protecting against accidental ingestion This study has several novel features which distinguish it from the two studies recently published on this topic and provides valuable new information. We employed a gradual updosing regime, compared to previously published rush or semi-rush studies [14, 16]. We also used a higher top immunotherapy maintenance dose (800 mg compared to 300 mg [14] or 125 mg [16]). Also, in demonstrating desensitisation we used a more rigorous final challenge with higher peanut dose than employed in previous studies (6.6 g protein, compared to 2 g [16], or 3.9 g [14]), ensuring detection of very high thresholds. We also identified that pre-OIT peanut-specific IgE may be a useful marker to stratify subjects into those who could be desensitised with relative ease and those who have greater difficulty. We performed threshold challenges before commencing immunotherapy and used these to guide the OIT starting dose [14]. Important new data on reactions due to extrinsic factors are described in the context of the overall safety data, which will inform future immunotherapy study design.

Our regime was well tolerated by participants (table 3). Two other groups have used more rapid updosing schedules, one had a seven day rush protocol to a planned top dose of approximately 125 mg protein followed by a slower updosing for those who did not achieve this [16]. 74% failed to increase their threshold during the rush period, but after gradual updosing 15/23 (65%) could tolerate 200 mg-2000 mg peanut. Overall 35% (8/23) dropped out. Jones et al employed a one day rush to 50 mg peanut protein with a planned top dose of 300 mg maintenance [14]. 74% failed to reach the intended top rush dose of 50 mg peanut and 10% required adrenaline; overall 34% (10/29) withdrew from the study. Only 11/39 (28%) eventually passed a 3.9 g peanut challenge with no symptoms. To contrast, we found that 19/22 (86%) tolerated gradual updosing to 800 mg protein, with a good safety profile and only one withdrawal (table 2). (64%) passed a final 6.6 g peanut challenge with no reaction. A rush protocol has the advantage of reducing the number of updosing appointments but these studies suggest that such protocols are poorly tolerated and not particularly effective. Further study of rush protocols under anti-IgE cover is warranted.

We used a higher top maintenance dose than previous studies (800 mg protein v 300 mg [14] and 125 mg [16]), meaning our subjects tolerated a greater amount of peanut and received a larger cumulative dose during immunotherapy. In subcutaneous immunotherapy, a higher immunotherapy dose is related to improved efficacy and this may help to explain the difference in outcome between studies. In our participants, OIT conferred protection against a minimum of 1.5 peanuts-much more than is likely to be encountered during accidental ingestion. For the majority their tolerated dose was raised beyond 6.6 g protein during challenge (14/22: 63%), a threshold higher than any previous study (3.9 g and 2.0 g protein) [14,16]. It was previously not known whether immunotherapy completely ablated reactivity, or simply raised the reactive threshold to a level somewhere above the immunotherapy dose. Using a lower cumulative challenge dose may not detect this increased threshold as 10-15% of peanut allergic subjects may still react to a higher dose [19].

This intervention would be most valuable to children with severe peanut allergy and/or low dose thresholds. The study sample included children with typical peanut allergy, representative of most degrees of severity and threshold dose, with sensitisation to the major peanut allergen (Ara h 2—table 2). Several children with a history of anaphylaxis were included. OIT with home dosing was well tolerated by the 14% with a history of anaphylaxis and 8/22 with a very low threshold dose of 1 mg peanut protein.

The duration of OIT was shortened if the immunotherapy starting dose was high (subjects with higher dose thresholds were commenced on higher initial OIT doses) and lengthened if there was difficulty in up dosing. The majority of participants tolerated the repeated planned dose increases and completed the protocol without major difficulty. A degree of flexibility in updosing is required because of differences in individual response to immunotherapy. Where reactions occurred on updosing, the dose was transiently reduced, but most continued to complete the protocol.

It would be desirable to identify characteristics in advance of performing immunotherapy which predict ease of desensitisation or risk of reactions. Alternative strategies could then be employed (e.g. more gradual dose increases). In this respect the dose threshold was not helpful in predicting outcome. However, no subject with a peanut serum specific IgE<27.3 kU/l required alteration to their immunotherapy dose (8/8), so an IgE below this level may be associated with ease of immunotherapy. Further, subjects who failed or could not attempt the final peanut challenge had a significantly higher peanut specific IgE than those who passed.

In summary using a new high-dose immunotherapy protocol with gradual dose increases we have shown that OIT is well tolerated and effective in typical peanut allergic patients, with improved outcome and acceptability. New information on updosing, use of peanut IgE to predict ease of desensitisation and individualization of treatment for 'standard' and 'difficult to desensitize' patients has been provided. We have also revealed interesting safety data regarding reactions with extrinsic factors during immunotherapy. Overall we have demonstrated it is possible to achieve an apparent 1000-fold increase in median tolerated dose of peanut protein by using OIT to treat children with peanut allergy.

REFERENCES

1. Grundy J, et al J Allergy Olin Immunol 2002; 110:784-9.
2. Sicherer S H, et al. J Allergy Olin Immunol 2003; 112:1203-7.
3. Kanny G et al J Allergy Clin Immunol 2001; 108:133-40.
4. Ho M H et al. J Allergy Clin Immunol 2008; 121:731-6
5. Primeau M N et al. Clin Exp Allergy 2000; 30:1135-43.
6. Avery N J et al. Ped Allergy Immunol 2003: 14: 378-382
7. Kapoor S et al Allergy 2004; 59:185-91.
8. Clark A T, Ewan P W. J Allergy Clin Immunol 2008; 122:286.
9. Ferdman R M et al Ann Allergy Asthma Immunol 2006; 97:73-7.

10. Oppenheimer J J et al. J Allergy Clin Immunol 1992; 90:256
11. Buchanan A D et al J Allergy Clin Immunol 2007; 119:199-205.
12. Longo G et al J Allergy Clin Immunol 2008; 121:343-7.
13. Enrique E et al Ann Allergy Asthma Immunol 2008; 100:283-4.
14. Jones S M et al J Allergy Olin Immunol. 2009; 124: 292-300
15. Hofmann A M et al J Allergy Clin Immunol. 2009; 124:286-91,
16. Blumchen K et al J Allergy Clin Immunol 2010; 126: 83-91.
17. Clark A T et al Allergy 2009; 64:1218-20.
18. Taylor S L et al Clin Exp Allergy 2004; 34:689-95.
19. Taylor S L et al Food Chem Toxicol 2010 March; 48(3):814-9
20. Pamphrey R S et al J Allergy Clin Immunol 2007; 119:1018-9
21. Anagnostou K et al Clin Exp Allergy 2011; 41: 1273-81

TABLE 1

| Male: female ratio | 1 | |
|---|---|---|
| Age at first peanut reaction | 2 years (0.3-7 years) | |
| Age at enrollment | 11 years (4-18 years) | |
| Other allergic disease | Active (%) | Outgrown (%) |
| Asthma | 64 | 9 |
| Rhinitis | 45 | 5 |
| Eczema | 36 | 45 |
| Egg allergy | 9 | 36 |
| Milk allergy | 5 | 23 |
| Severity of worst reaction before enrollment | Mild | 23% |
| | Moderate | 36% |
| | Severe | 14% |
| | Unclassified* | 27% |

Numbers are median (range) unless otherwise specified.
Age is shown in years.
*Clinical details insufficient to classify.

TABLE 3

| | Updosing phase | | Maintenance phase | |
|---|---|---|---|---|
| | n | % | n | % ($\times 10^{-2}$) |
| Total number of doses | 2920 | | 5406 | |
| Symptoms | | | | |
| Sore throat | 14 | 0.5 | 0 | 0 |
| Erythema | 3 | 0.1 | 3 | 0.05 |
| Urticaria | 4 | 0.1 | 17 | 0.3 |
| Angioedema | 7 | 0.2 | 1 | 0.02 |
| Conjunctivitis | 7 | 0.2 | 0 | 0 |
| Rhinitis | 11 | 0.4 | 0 | 0 |
| Cough | 0 | 0 | 2 | 0.04 |
| Wheeze | 11 | 0.4 | 17 | 0.3 |
| Oral Itching | 138 | 5 | 40 | 0.7 |
| Nausea | 32 | 1 | 2 | 0.04 |
| Vomiting | 19 | 0.7 | 0 | 0 |
| Abdominal pain | 115 | 4 | 31 | 0.6 |
| Treatment | | | | |
| None | 104 | 4 | 27 | 0.5 |
| AH alone | 213 | 7 | 53 | 0.9 |
| Inhaled salbutamol alone | 1 | 0.04 | 1 | 0.02 |
| AH + inhaled salbutamol | 10 | 0.4 | 16 | 0.3 |
| IM adrenaline | 0 | 0 | 0 | 0 |

TABLE 2

| Subject number | Peanut specific IgE (kU/l) | Ara h 2-specific IgE (kU/l) | Maximum-tolerated dose pre-OIT (mg) | Pre-OIT challenge symptoms* | Starting dose of OIT (mg) | Maximum-tolerated peanut after OIT (mg) | Number of transient dose reductions during OIT |
|---|---|---|---|---|---|---|---|
| 1 | 253 | 70.4 | 81 | OI, TC, A, U, AP, N | 5 | 3278 | 3 |
| 2 | 3.81 | 0.57 | 75 | TC, AP | 1 | 6354 | 0 |
| 3 | 5.17 | 2.91 | 110 | OI, RC | 5 | 6602 | 0 |
| 4 | 27.3 | 21.0 | 1 | OI, RC | 0.5 | 6574 | 2 |
| 5 | 46 | 21.3 | 1 | OI, A | 0.5 | 6886 | 0 |
| 6 | 29.7 | 15.8 | 6 | OI, AP | 1 | 6503 | 2 |
| 7 | 3.49 | 0.38 | 6 | OI, BC, A, AP | 1 | 6486 | 0 |
| 8 | 6.44 | 3.73 | 81 | AP | 25 | 7510 | 0 |
| 9 | 16.1 | 5.25 | 75 | OI, E, U, AP, N | 50 | 5674 | 0 |
| 10 | 287 | >100 | 31 | OI, E, AP, N | 5 | 6663 | 2 |
| 11 | 1.54 | 1.41 | 1 | OI | 0.5 | 6801 | 0 |
| 12 | 194 | NA | 56 | SOB, N, AP | 6 | 6411 | 4 |
| 13 | 433 | >100 | 1 | OI, A, E | 0.5 | 2485 | 0 |
| 14 | 395 | >100 | 1 | OI, E | 0.5 | 2443 | 0 |
| 15 | 77.0 | 75.3 | 1 | OI, TC | 0.5 | 6250 | 0 |
| 16 | 4.25 | NA | 55 | OI, E | 5 | 6654 | 0 |
| 17 | 31.3 | 29.1 | 1 | OI, RC, AP, N, V | 0.5 | 800 | 2 |
| 18 | 0.41 | <0.35 | 100 | OI, TC, AP | 5 | 6459 | 0 |
| 19 | 65.1 | 53.6 | 6 | OI, TC, AP, V | 0.5 | 6500 | 0 |
| 20 | 354 | NA | 1 | OI | 0.5 | 800 | 9 |
| 21 | 800 | >100 | 81 | RC, AP, V | 5 | 800 | 7 |
| 22 | 14.3 | NA | 81 | Dropout | 25 | Dropout | Dropout |

*All symptoms occurred on active challenge arm. There were no placebo reactions.
NA, not available. Challenge symptoms: OI, oral itching; TC, throat closing; A, angioedema; U, urticaria; E, erythema; AP, abdominal pain with significant change in behavior; N, nausea; V, vomit; SOB, short of breath; W, wheeze; RC, rhinoconjunctivitis; OIT, oral immunotherapy.

TABLE 4

| | Extrinsic factors | | | | | | | |
|---|---|---|---|---|---|---|---|---|
| Subject # | Infection or other intercurrent illness | Exercise | Tiredness | Anxiety | Aero-allergen co-exposure | Menstruation | Total number of episodes | Symptoms |
| 1 | | 1 | | | 2 | | 3 | RC, W |
| 4 | 1 | | 3 | 1 | | | 5 | OI, W, SOB |
| 5 | | | 1 | | | | 1 | OI |
| 6 | 1 | 1 | >5 | | | | >5 | AP, V, A |
| 7 | | | 5 | | | | 5 | AP, RC, OI |
| 12 | | | | 1 | | | 1 | AP, W |
| 14 | 4 | | | | | | 4 | OI, AP, W |
| 15 | >5 | | | | | | >5 | OI |
| 17 | 1 | | >5 | | | | >5 | AP, N |
| 19 | 1 | 4 | 2 | | | | >5 | W, V |
| 20 | >5 | | 2 | | >5 | | >5 | OI, AP |
| 21 | >5 | | 1 | | | 3 | >5 | AP, U, W |

TABLE 5

| | Passed 30 week challenge n = 14 | Failed 30 week challenge n = 7 | p value |
|---|---|---|---|
| Pre-OIT challenge threshold (mg) | 31 (1-110) | 1 (1-81) | ns |
| Serum peanut IgE (kU/l) | 6.44 (0.41-287) | 354 (31.3-800) | 0.0025* |
| Serum Ara h 2 (kU/l) | 10.5 (0.35-≥100) | ≥100 (29.1-≥100) | 0.0087* |
| Age (y) | 12 (7-18) | 9 (4-13) | ns |
| Current rhinitis | 10 (71%) | 4 (57%) | ns |
| Current asthma | 6 (43%) | 4 (57%) | ns |

The invention claimed is:

1. A method of treating an individual with peanut allergy which comprises:
   (1) orally administering a series of daily oral doses of peanut protein to the individual with peanut allergy, beginning with an initial daily oral dose and then increasing to a maximum daily oral dose, wherein the series of daily oral doses consists of doses consisting of 2 mg, 5 mg, 12.5 mg, 25 mg, 50 mg, 100 mg and 200 mg of peanut protein, and wherein each of the doses in the series of daily oral doses is increased after at least 2 weeks of daily administration until the maximum daily oral dose in the series of daily oral doses is reached, and
   (2) orally administering the maximum daily oral dose in the series of daily oral doses to the individual with peanut allergy daily for at least 1 year.

2. The method according to claim 1 wherein the peanut protein is administered as peanut flour.

3. The method according to claim 2 wherein the peanut flour is admixed with a carrier for administration.

4. The method according to claim 3 wherein the carrier is a dairy or dairy substitute product.

5. The method according to claim 1, further comprising measuring levels of anti-peanut IgE in the serum of the individual with peanut allergy, wherein the level of anti-peanut IgE in the serum of the individual is reduced or eliminated by the treatment.

* * * * *